United States Patent [19]

Suresh et al.

[11] 4,413,155

[45] Nov. 1, 1983

[54] AMMOXIDATION OF OLEFINS WITH NOVEL ANTIMONATE CATALYSTS

[75] Inventors: Dev D. Suresh, Macedonia; Robert K. Grasselli, Chagrin Falls; David A. Orndoff, Windsor, all of Ohio

[73] Assignee: The Standard Oil Co., Cleveland, Ohio

[21] Appl. No.: 249,034

[22] Filed: Mar. 30, 1981

Related U.S. Application Data

[60] Continuation of Ser. No. 108,326, Dec. 31, 1979, abandoned, which is a division of Ser. No. 57,853, Jul. 16, 1979, abandoned, which is a continuation-in-part of Ser. No. 862,268, Dec. 20, 1977, abandoned.

[51] Int. Cl.$^3$ .............................................. C07C 11/12
[52] U.S. Cl. .................. 585/417; 260/465.3; 585/431; 585/616; 585/621; 585/622; 585/623; 585/624; 585/625; 585/626; 585/631
[58] Field of Search ............... 585/431, 418, 616, 621, 585/622, 623, 624, 625, 626, 631, 417

[56] References Cited

U.S. PATENT DOCUMENTS

| | | | |
|---|---|---|---|
| 3,642,930 | 2/1972 | Grasselli et al. | 585/626 X |
| 3,658,877 | 4/1972 | Callahan et al. | 585/626 X |
| 3,716,496 | 2/1973 | Yoshino et al. | 585/626 X |
| 3,764,632 | 10/1973 | Takenaka et al. | 585/626 X |
| 3,801,670 | 4/1974 | Shiraishi et al. | 585/626 |
| 3,825,502 | 7/1974 | Takenaka et al. | 585/626 X |
| 3,911,039 | 10/1975 | Grasselli et al. | 585/626 |
| 3,932,551 | 1/1976 | Grasselli et al. | 585/626 X |
| 3,972,920 | 8/1976 | Ishii et al. | 585/626 X |
| 4,035,418 | 7/1977 | Okada et al. | 585/626 X |
| 4,174,354 | 11/1979 | Grasselli et al. | 585/626 |

*Primary Examiner*—Thomas A. Waltz
*Attorney, Agent, or Firm*—J. E. Miller, Jr.; H. D. Knudsen; L. W. Evans

[57] ABSTRACT

Oxide complex catalysts comprising Fe-Sb-Bi-O$_x$ promoted with a wide variety of different elements have been found to be especially useful in the ammoxidation of olefins to nitriles such as acrylonitrile and methacrylonitrile. Not only are the desired nitriles obtained with high yields when these catalysts are used, but also the production of unwanted liquid byproducts such as acrolein, acrylic acid and acetonitrile is significantly reduced.

5 Claims, No Drawings

AMMOXIDATION OF OLEFINS WITH NOVEL ANTIMONATE CATALYSTS

REFERENCE TO RELATED APPLICATIONS

This application is a continuation application of prior application Ser. No. 108,326, filed Dec. 31, 1979, which is a division of prior application Ser. No. 57,853, filed July 16, 1979, which is a continuation-in-part of prior application Ser. No. 862,268, filed Dec. 20, 1977, all now abandoned.

BACKGROUND OF THE INVENTION

The present invention relates to a novel catalyst and process for the catalytic vapor phase ammoxidation of olefins to nitriles using antimonate catalysts.

U.S. Pat. No. 3,716,496 discloses a catalyst useful for the ammoxidation of olefins to nitriles having the formula

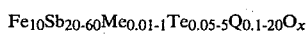

$$Fe_{10}Sb_{20-60}Me_{0.01-1}Te_{0.05-5}Q_{0.1-20}O_x$$

wherein
  Me is an element selected from the group consisting of V, Mo and W and
  Q is an element selected from the group consisting of Cu, Ag, Be, Mg, Ca, Sr, Ba, Zn, Cd, La, Ce and Al.
Netherlands Pat. No. 7,501,472 discloses similar catalysts, these catalysts also containing at least one of P and B.

In commercial vapor phase processes for producing acrylonitrile, a liquid reaction product containing acrolein, acrylic acid and acetonitrile as well as acrylonitrile is normally obtained. It is oftentimes difficult to separate acrolein, acrylic acid and/or acetonitrile from this liquid reaction product, and hence processes yielding these unwanted liquid byproducts in significant amounts are disadvantageous commercially. Unfortunately, vapor phase ammoxidation processes using promoted Fe-Te-Sb-$O_x$ catalysts do yield these unwanted byproducts in significant amounts. Furthermore, tellurium in such catalysts tends to volatilize as tellurium oxide, which leads not only to a significant decrease in catalytic activity with time but also to significant pollution problems.

Accordingly, it is an object of the present invention to provide a novel process for the ammoxidation of olefins to nitriles in which the production of acrolein, acrylic acid and acetonitrile is significantly reduced by means of a catalyst not containing tellurium as an essential component.

SUMMARY OF THE INVENTION

These and other objects are accomplished by the present invention in accordance with which olefins, in particular propylene and isobutylene, are catalytically ammoxidized with an oxidation catalyst comprising an oxide complex of an Fe-Bi-Sb-$O_x$-based catalyst promoted with at least one element selected from the group consisting of Cu, Ce, U, V, Cr, Mn, Co, Ni, Zn, Cd, rare earth, Ca, In, Tl, Th, Mo, W, Nb, Ta, Sn, Ge, P, B, and As. In accordance with the present invention, it has been found that the production of acrolein, acrylic acid and/or acetonitrile can be significantly reduced when catalysts of this type are employed.

Thus, the present invention provides a novel catalyst useful in the ammoxidation of various compounds to nitriles, the catalyst comprising a uranium and tellurium-free oxide complex of the following general formula

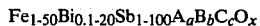

$$Fe_{1-50}Bi_{0.1-20}Sb_{1-100}A_aB_bC_cO_x$$

wherein
  A is Cu, Ce, V, Cr and/or Mn;
  B is alkali metal, earth alkali, Co, Ni, Zn, Cd, rare earth metal other than Ce, Ga, In, Tl and/or Th;
  C is Mo, W, Nb, Ta, Sn, Ge, Ti, Zr, P, B and/or As; and
wherein
  a is 0.01 to 20;
  b is 0 to 20;
  c is 0.01 to 20;
  x is a number determined by the oxygen requirements of the other elements present; and
wherein the amount of Sb in said catalyst on an atomic basis is greater than the sum of the amounts of all other elements in said catalyst excluding oxygen.

In addition, the present invention also provides a novel ammoxidation process in which an olefin together with oxygen and ammonia is contacted with a catalyst of the above composition at elevated temperature.

In accordance with another aspect of the present invention it has also been found that various aldehydes and acids can be ammoxidized with the inventive catalysts, and thus the present invention includes ammoxidation processes of the type described above in which the feed comprises an aldehyde and/or alcohol rather than an olefin.

Finally it has also been found that the catalysts of the present invention are effective in the oxidation of various olefins to oxygenated compounds and the oxydehydrogenation of various olefins to diolefins. Thus, the present invention provides two additional processes for the oxidation and oxydehydrogenation of olefins in which the olefin to be reacted together with oxygen is contacted with a catalyst of the formula given above.

DETAILED DESCRIPTION

The novel catalyst of the present invention finds significant use in the ammoxidation of olefins to nitriles. They can also be used, however, in the ammoxidation of alcohols and aldehydes to nitriles as well as in the oxidation of olefins to oxygenated compounds and the oxidative dehydrogenation of olefins to diolefins and aromatics.

Ammoxidation

A wide variety of different reactants can be ammoxidized in accordace with the present invention to produce nitriles. For example, olefins such as propylene and isobutylene, alcohols such as t-butyl alcohol, and aldehydes such as acrolein and methacrolein can be readily converted to nitriles in accordance with the present invention. In general, compounds which can be converted to nitriles by the inventive ammoxidation reaction include 3 to 9 carbon atom hydrocarbons unsubstituted or substituted with oxygen or hydroxy. Preferred starting materials are olefins, aldehydes and alcohols containing 3 or 4 carbon atoms.

The general ammoxidation process for converting olefins, alcohols and aldehydes to nitriles is well known. See, for example, U.S. Pat. No. 3,546,138, the disclosure of which is incorporated herein by reference. In general, the ammoxidation reaction is accomplished by contacting the reactant, oxygen and ammonia with a particular catalyst in the vapor phase. The inventive reaction is carried out in the same manner and under the conditions generally set forth in this patent.

In a preferred aspect, the inventive process comprises contacting a mixture comprising propylene or isobutylene, ammonia and oxygen with the promoted catalyst of this invention at an elevated temperature and at atmospheric or near atmospheric pressure.

Any source of oxygen may be employed in this process. For economic reasons, however, it is preferred that air be employed as the source of oxygen. From a purely technical viewpoint, relatively pure molecular oxygen will give equivalent results. The molar ratio of oxygen to the olefin in the feed to the reaction vessel should be in the range of 0.5:1 to 4:1 and a ratio of about 1:1 to 3:1 is preferred.

Low molecular weight saturated hydrocarbons do not appear to influence the reaction to an appreciable degree, and these materials can be present; consequently, the addition of saturated hydrocarbons to the feed to the reaction is contemplated within the scope of this invention. Likewise, diluents, such as nitrogen and the oxides of carbon, may be present in the reaction mixture without deleterious effect.

The molar ratio of ammonia to olefin in the feed to the reactor may vary between about 0.05:1 to 5:1. There is no real upper limit for the ammonia/olefin ratio, but there is generally no reason to exceed the 5:1 ratio. At ammonia/olefin ratios appreciably less than the stoichiometric ratio of 1:1, various amounts of oxygenated derivatives of the olefin will be formed.

Significant amounts of unsaturated aldehydes, as well as nitriles, will be obtained at ammonia-olefin ratios substantially below 1:1, i.e., in the range of 0.15:1 to 0.75:1. Above the upper limit of this range, the amount of aldehydes produced rapidly decreases. It is fortuitous that within the ammonia-olefin range stated, maximum utilization of ammonia is obtained and this is highly desirable. It is generally possible to recycle any unreacted olefin and unconverted ammonia.

Water can also be included in the feed although it is not essential. In some instances, e.g., fixed-bed systems, water may improve the selectivity of the reaction and the yield of nitrile. However, reactions not including water in the feed are also within the scope of the present invention.

In general, the molar ratio of added water to olefin, when water is added, is in the neighborhood of 0.1:1 or higher. Ratios on the order of 1:1 to 3:1 are particularly desirable, but higher ratios may be employed, i.e., up to about 10:1.

The reaction is carried out at an elevated temperature such as 200°–600° C., preferably 400°–500° C. The pressure at which the reaction is conducted is also an important variable, and the reaction should be carried out at about atmospheric or slightly above atmospheric (2 to 3 atmospheres) pressure. In general, high pressures, i.e. above 15 atmospheres, are not suitable since higher pressures tend to favor the formation of undesirable byproducts.

The apparent contact time is not critical, and contact times in the range of from 0.1–50 seconds may be employed. The optimal contact time will, of course, vary depending upon the reactant being used, but in general, contact time of from 1–15 seconds is preferred.

The inventive ammoxidation reaction is carried out in the vapor phase. Normally, the process is conducted on a continuous basis using either a fixed-bed or a fluid-bed catalyst. However, a batch operation can be employed.

The reaction product passing out of the reactor is normally in the form of a gas. Conventionally, this gaseous reaction product is treated to remove $NH_3$ and then partially condensed either by indirect contact with a cooling medium or direct contact with water to form a liquid phase containing acrylonitrile, acrolein, acrylic acid, HCN and acetonitrile and a vapor phase containing $CO_2$, CO, $N_2$ and $OH_2$. The acrylonitrile is then separated from the liquid phase by a number of different techniques such as, for example, distillation or water extraction/distillation. Additional steps can be employed to separately recover acrylic acid and/or acrolein from the gross reaction product.

In accordance with the present invention, the amount of acrolein, acrylic acid and acetonitrile produced by the inventive ammoxidation reaction are significantly reduced. Thus, separation of the acrylonitrile from the remaining components of the gross reaction product is simplified. Further, problems associated with disposing of the unwanted byproducts, such as water pollution, are greatly reduced.

Oxidation

As previously indicated, the catalysts of this invention can also be employed in the catalytic oxidation of olefins to various different reaction products.

The reactants used in the oxidation to oxygenated compounds are oxygen and an olefin such as propylene, isobutylene and other olefins having up to three contiguous carbon atoms (i.e. three carbon atoms arranged in a straight chain).

The olefins may be in admixture with paraffinic hydrocarbons, such as ethane, propane, butane and pentane; for example, a propylene-propane mixture may constitute the feed. This makes it possible to use ordinary refinery streams without special preparation.

The temperature at which this oxidation is conducted may vary considerably depending upon the catalyst, the particular olefin being oxidized and the correlated conditions of the rate of throughput or contact time and the ratio of olefin to oxygen. In general, when operating at pressures near atmospheric, i.e., 0.1–10 atmospheres, temperatures in the range of 150° C.–600° C. may be advantageously employed. However, the process may be conducted at other pressures, and in the case where superatmospheric pressures, e.g., above 10 atmospheres are employed, somewhat lower temperatures are possible. In the case where this process is employed to convert propylene to acrolein, a temperature range of 200° C.–500° C. has been found to be optimum at atmospheric pressure.

While pressures other than atmospheric may be employed, it is generally preferred to operate at or near atmospheric pressure, since the reaction proceeds well at such pressures and the use of expensive high pressure equipment is avoided, and formation of undesired byproducts and waste is diminished.

The apparent contact time employed in the process is not critical and it may be selected from a broad operable range which may vary from 0.1 to 50 seconds. The apparent contact time may be defined as the length of time in seconds which a unit volume of gas measured under the conditions of reaction is in contact with the apparent unit volume of the catalyst. It may be calculated, for example, from the apparent volume of the catalyst bed, the average temperature and pressure of the reactor, and the flow rates of the several components of the reaction mixture.

The optimum contact time will, of course, vary depending upon the olefin being treated, but in the case of propylene and isobutylene, the preferred contact time is 0.15 to 15 seconds.

A molar ratio of oxygen to olefin between about 0.5:1 to 5:1 generally gives the most satisfactory results. For the conversion of propylene to acrolein, a preferred ratio of oxygen to olefin is from about 1:1 to about 2:1. The oxygen used in the process may be derived from any source; however, air is the least expensive source of oxygen and is preferred for that reason.

The addition of water to the reaction mixture in oxidation reactions can have a beneficial influence on the conversion and yields of the desired product especially in fixed-bed reactions. The manner in which water affects the reaction is not fully understood. In any event, it is preferred in fixed-bed operation to include water in the reaction mixture, and in general a ratio of olefin to water in the reaction mixture of from 1:0.25 to 1:10 will give very satisfactory results while a ratio of 1:0.5 to 1:6 has been found the optimum when converting propylene to acrolein.

Inert diluents such as oxygen and carbon dioxide, may be present in the reaction mixture.

Oxydehydrogenation

In accordance with the present invention, the promoted catalyst system of the present invention can also be employed in the catalytic oxidative dehydrogenation of olefins to diolefins and aromatic compounds. In this process, the feed stream in vapor form containing the olefin to be dehydrogenated and oxygen is conducted over the promoted catalyst at a comparatively low temperature to obtain the corresponding diolefin.

By the term "olefin" as used herein is meant open chain as well as cyclic olefins. The olefins dehydrogenated in accordance with this invention have at least four and up to about nine nonquaternary carbon atoms, of which at least four are arranged in series in a straight chain or ring. The olefins preferably are either normal straight chain or tertiary olefins. Both cis and trans isomers, where they exist, can be dehydrogenated.

Among the many olefinic compounds which can be dehydrogenated in this way are butene-1; butene-2; pentene-1; pentene-2; pentenes, hexenes, etc. such as 2-methyl-pentene-1, 3-methylbutene-1, 3,4-dimethylpentene-1, 4-methyl-pentene-2; heptene-1; octene-1; cyclopentene; cyclohexene; 3-methyl cyclohexene and cycloheptene.

Open chain olefins yield diolefins, and, in general, six-membered ring olefins yield aromatic ring compounds. The higher molecular weight open chain olefins may cyclize to aromatic ring compounds.

The feed stock in addition to the olefin and oxygen can contain one or more paraffinic or naphthenic hydrocarbons having up to about ten carbon atoms, which may be present as impurities in some petroleum hydrocarbon stocks and which may also be dehydrogenated in some cases.

The amount of oxygen can be within the range of from about 0.3 to about 4 moles per mole of double-bond created. Stoichiometrically, 0.5 mole of oxygen is required for the dehydrogenation of one mole of a monoolefin to a diolefin. It is preferred to employ an excess of oxygen, e.g. an oxygen/olefin ratio of from 0.6 to about 3, in order to ensure a higher yield of diolefin per pass. The oxygen can be supplied as pure or substantially pure oxygen or as air or in the form of hydrogen peroxide.

When pure oxygen is used, it may be desirable to incorporate a diluent in the mixture such as steam, carbon dioxide or nitrogen.

The feed stock is preferably catalytically dehydrogenated in the presence of steam, but this is not essential. Usually, from about 0.1 to about 6 moles of steam per mole of olefin reactant is employed, but amounts larger than this can be used.

The dehydrogenation proceeds at temperatures within the range of from about 300° C. to about 1000° C. Optimum yields are obtainable at temperatures within the range from about 400° to 550° C. However, since the reaction is exothermic, temperatures in excess of 550° C. should not be used, unless means are provided to carry off the heat liberated in the course of the reaction. Due to the exothermic nature of the reaction, the temperature of the gaseous reaction mixture will be higher than the temperature of the feed entering the system by as much as 75° C. The temperatures referred to are those of the entering gas feed near the reactor inlet.

The preferred reaction pressure is approximately atmospheric, within the range of from about 0.1 to about 5 atmospheres.

Only a brief contact time with the catalyst is required for effective dehydrogenation. The apparent contact time with the catalyst can vary from about 0.5 up to about 50 seconds but higher contact times can be used if desired. At these contact times, comparatively small reactors and small amounts of catalyst can be used effectively.

Process Conditions

In carrying out the foregoing processes, any apparatus of the type suitable for carrying out oxidation reactions in the vapor phase may be employed. The processes may be conducted either continuously or intermittantly. The catalyst may be a fixed-bed employing a large particulate or pelleted catalyst or, in the alternative, a fluid-bed catalyst may be employed.

Catalyst

The catalysts employed in accordance with the present invention are uranium and tellurium-free oxide complexes of iron, bismuth and antimony promoted with various additional elements and can be described by the following general formula:

$$Fe_{1-50}Bi_{0.1-20}Sb_{1-100}A_aB_bC_cO_x$$

wherein
A is Cu, Ce, V, Cr and/or or Mn;
B is alkali metal, earth alkali, Co, Ni, Zn, Cd, rare earth metal other than Ce, Ga, Zn, Tl and/or Th;
C is Mo, W, Nb, Ta, Sn, Ge, Ti, Zr, P, B and/or As; and wherein
a is 0.01 to 20;
b is 0 to 20;
c is 0.01 to 20;
x is the number determined by the oxygen requirement of the other elements present; and
wherein the amount of Sb in said catalyst on an atomic basis is greater than the sum of the amounts of all other elements in said catalyst excluding oxygen.

Of the foregoing catalysts, those which contain both A and C elements are preferred. In addition, catalysts containing Mo, W, Nb and/or Ta are especially preferred. Catalysts in which C is a mixture of Mo and W are most preferred.

These catalysts can be used either in unsupported form or supported on suitable carriers such as $SiO_2$, $Al_2O_3$, $BPO_4$, $SbPO_4$, $ZrO_2$, Alundum and the like. The catalysts can also be coated on these supports by special techniques known in the art.

These catalysts can be prepared by conventional techniques. In this regard, U.S. Pat. No. 3,546,138, mentioned above, teaches how catalysts of this type can be made. Also see U.S. Pat. Nos. 3,461,150; 3,325,504; 3,933,751; 3,435,061; 3,431,292 and 3,308,151, the disclosures of which are incorporated herein by reference, which also disclose how catalysts of this general type can be made.

added to the Fe/W solution, and so forth until an aqueous solution containing Fe, W, Mo, Bi and Cu was obtained. To this salt solution was added 72.87 grams $Sb_2O_3$ which had been slurried in about 400 ml. concentrated $NHO_3$ at 60°–70° C. for 1½ hours. Sufficient reagent grade $NH_4OH$ (about 150 cc) was then added to the mixture to adjust the pH to 2.0 and the mixture was then evaporated to dryness. The dried precipitation was heat treated in air for 3 hours at 290° C. and then for 3 more hours at 425° C. The resultant material was then screened to 20–35 mesh to produce the objective catalyst.

5 cc's. of this catalyst was charged into a fixed-bed reactor, and a feed comprising 1 propylene/1.1 $NH_3$/10.6 air/4$H_2O$ was fed to the reactor at elevated temperature. The reaction temperature and the contact time were varied from example to example. The gross reaction product was recovered and analyzed. The results obtained are set forth in the following Table I.

TABLE I $W_{0.2}Mo_1Bi_2Cu_3Fe_{12}Sb_{25}O_x$ + 50% $SiO_2$

| Example | Contact Time (sec) | Reaction Temp. °C. | % Yield Unreacted Propylene | Acrylonitrile | Acrolein | Acrylic Acid | Aceto-nitrile | HCN | CO | $CO_2$ | % AN Selectivity |
|---|---|---|---|---|---|---|---|---|---|---|---|
| 1 | 3 | 430 | 11.8 | 67.0 | — | 0.3 | 1.1 | 5.5 | 4.8 | 9.6 | 75.9 |
| 2 | 6 | 430 | 5.1 | 70.8 | — | 1.8 | 0.4 | 7.8 | 5.5 | 8.7 | 74.5 |
| 3 | 3 | 460 | 3.9 | 73.5 | — | 0.3 | 0.4 | 6.9 | 4.6 | 10.5 | 76.5 |

EXAMPLES

In order to more thoroughly describe the present invention, the following working examples in which propylene was ammoxidized to acrylonitrile are presented. In these examples, the term "% yield" means (moles product formed/moles reactant fed) × 100

EXAMPLES 1–3

50% $W_{0.2}Mo_1Bi_2Cu_3Be_{12}Sb_{25}O_x$ + 50% $SiO_2$

A catalyst of the aove formula was prepared by the following procedure.

96.96 grams $Fe(NO_3)_3.9H_2O$, 1.08 grams $(NH_4)_6W_7O_{24}.6H_2O$, 3.53 grams $(NH_4)_6Mo_7O_{24}.4H_2O$, 19.40 grams $Bi(NO_3)_3.5H_2O$ and 14.50 grams $Cu(NO_3)_2.3H_2O$ were individually dissolved in small amounts of water at 60° C. with stirring. The individual solutions were then added together in the order given above, i.e. the W-containing solution was first added to the Fe-containing solution, then the Mo solution was As will be noted from the foregoing experiments, acrylonitrile was produced in high yields with good selectivities. Moreover, the amounts of unwanted byproducts acrolein, acrylic acid and acetonitrile are very small. Thus, it will be appreciated that the present invention marks a significant improvement over many known processes for producing acrylonitrile which produce unwanted byproducts in significant amounts.

EXAMPLES 4–10

Additional experiments in which propylene was ammoxidized to acrylonitrile were conducted. These experiments were carried out in the same way as those of Examples 1 to 3 except that the feed consisted of 1.0 propylene/1.1 $NH_3$/10.6 air/4.0$H_2O$, the contact time was 3 seconds and the catalyst used was different. The compositions of the various catalysts used in these experiments as well as the results obtained are set forth in the following Table II.

TABLE II

| | | | % Propylene Conversion To | | | | |
|---|---|---|---|---|---|---|---|
| Example | Catalyst | Reaction Temp. °C. | Unreacted Propylene | Acrylo-nitrile | Acrolein | Acrylic Acid | Acetonitrile |
| 4 | $Fe_{12}Sb_{25}Cr_{0.2}Bi_2Cu_3Mo_1O_x$ + 40% $SiO_2$ | 460 | 12.2 | 60.2 | 9 | 0.5 | 1.9 |
| 5 | $Fe_{12}Sb_{25}Cr_{0.2}Bi_2Cu_3Mo_1O_x$ + 40% $SiO_2$ | 430 | 16.5 | 57.6 | 0 | 0.2 | 1.9 |
| 6 | $Fe_{12}Sb_{27}W_{0.2}Bi_2Cu_5Mo_1O_x$ + 40% $SiO_2$ | 460 | 22.1 | 43.1 | 3.5 | 0.2 | 2.3 |
| 7 | $Fe_{12}Sb_{25}W_{0.2}Bi_2Cu_3Mo_3O_x$ + 40% $SiO_2$ | 460 | 47.8 | 20.5 | 3.7 | 0.4 | 1.8 |
| 8 | $Fe_{12}Sb_{25}W_{0.2}Bi_2Cu_3Mo_3O_x$ + 40% $SiO_2$ | 430 | 39.3 | 29.2 | 0 | 1.1 | 5.1 |

| | | | % Propylene Conversion To | | | |
|---|---|---|---|---|---|---|
| Example | Catalyst | Reaction Temp. °C. | HCN | CO | $CO_2$ | % AN Selectivity |
| 4 | $Fe_{12}Sb_{25}Cr_{0.2}Bi_2Cu_3Mo_1O_x$ + 40% $SiO_2$ | 460 | 0.3 | 1.2 | 23.7 | 68.6 |
| 5 | $Fe_{12}Sb_{25}Cr_{0.2}Bi_2Cu_3Mo_1O_x$ + | 430 | 0.4 | 1.1 | 22.2 | 69.0 |

TABLE II-continued

| Example | Catalyst | | | | |
|---|---|---|---|---|---|
| 6 | $Fe_{12}Sb_{27}W_{0.2}Bi_2Cu_5Mo_1O_x$ + 40% $SiO_2$ | 460 | 0.3 | 0.4 | 28.1 | 55.4 |
| 7 | $Fe_{12}Sb_{25}W_{0.2}Bi_2Cu_3Mo_3O_x$ + 40% $SiO_2$ | 460 | 0.3 | 6.3 | 19.2 | 39.3 |
| 8 | $Fe_{12}Sb_{25}W_{0.2}Bi_2Cu_3Mo_3O_x$ + 40% $SiO_2$ | 430 | 5.1 | 9.6 | 10.6 | 48.2 |

| | | | % Propylene Conversion To | | | |
|---|---|---|---|---|---|---|
| Example | Catalyst | Reaction Temp. °C. | Unreacted Propylene | Useful Liquid Product* | CO + $CO_2$ | Selectivity to Useful Products |
| 9 | $Mn_{12}Sb_{27}W_{0.2}Bi_2Cu_5Mo_1O_x$ + 40% $SiO_2$ | 400 | 58.8 | 10.8 | 30.4 | 26.2 |
| 10 | $Mn_{12}Sb_{27}W_{0.2}Bi_2Cu_5Mo_1O_x$ + 40% $SiO_2$ | 430 | 61.1 | 8.3 | 30.6 | 21.4 |

*Useful Liquid Product contains primarily acrylonitrile.

Although only a few embodiments of the present invention have been discussed above, it should be appreciated that many modifications can be made without departing from the spirit and scope of the invention. All such modifications are intended to be included within the scope of the present invention, which is to be limited only by the following claims.

We claim:

1. In an oxydehydrogenation process wherein an olefin having four or more contiguous carbon atoms and oxygen are contacted at elevated temperature in the vapor phase with a catalyst, the improvement wherein said catalyst is free of uranium and tellurium and defined by the following general formula:

$$Fe_{1-50}Bi_{0.1-20}Sb_{1.12-100}A_aB_bC_cO_x$$

wherein

A is at least Cu and optionally Ce, V, Cr and/or Mn;
B is earth alkali, Co, Ni, Zn, Cd, rare earth metal other than Ce, Ga, In, Tl and/or Th;
C is Mo, W, Nb, Ta, Sn, Ge, Ti, Zr, P, B and/or As; and wherein a is 0.01 to 20;
b is 0 to 20;
c is 0.01 to 20;
x is a number determined by the oxygen requirements of the other elements present; and wherein the amount of Sb in said catalysts on an atomic basis is greater than the sum of the amounts of all other elements in said catalyst excluding oxygen.

2. The process of claim 1 wherein C is at least one of Mo, W, Nb and Ta.

3. The process of claim 1 wherein said catalyst contains both Mo and W.

4. The process of claim 1 wherein said catalyst contains Mo.

5. The process of claim 1 wherein b is greater than 0.

* * * * *